US006663592B2

(12) United States Patent
Rhad et al.

(10) Patent No.: US 6,663,592 B2
(45) Date of Patent: Dec. 16, 2003

(54) CATHETER INTRODUCER ASSEMBLY HAVING SAFETY SHIELDED NEEDLE

(75) Inventors: Edward A. Rhad, Fairfield, OH (US); Mark Tsonton, Loveland, OH (US); Randy R. Stephens, Fairfield, OH (US); Malcolm L. Russelburg, Blanchester, OH (US)

(73) Assignee: Medex, Inc., Carlsbad, CA (US)

( * ) Notice: Subject to any disclaimer, the term of this patent is extended or adjusted under 35 U.S.C. 154(b) by 146 days.

(21) Appl. No.: 09/948,088

(22) Filed: Sep. 6, 2001

(65) Prior Publication Data
US 2003/0060769 A1 Mar. 27, 2003

(51) Int. Cl.[7] .......................... A61M 5/00; A61M 5/178
(52) U.S. Cl. ................... 604/110; 604/164.01; 128/919
(58) Field of Search ............................. 604/93.01, 110, 604/164.01, 164.06, 164.07, 164.08, 187, 192, 263, 264, 272; 128/919

(56) References Cited

U.S. PATENT DOCUMENTS

| 4,790,828 A | 12/1988 | Dombrowski et al. |
| 4,828,547 A | 5/1989 | Sahi et al. |
| 4,929,241 A | 5/1990 | Kulli |
| 4,952,207 A | 8/1990 | Lemieux |
| 4,964,854 A | 10/1990 | Luther |
| 4,978,344 A | 12/1990 | Dombrowski et al. |
| 4,994,041 A | 2/1991 | Dombrowski et al. |
| 5,000,740 A | 3/1991 | Ducharme et al. |
| 5,009,642 A | 4/1991 | Sahi |
| 5,053,017 A | 10/1991 | Chamuel |
| 5,085,648 A | 2/1992 | Purdy et al. |
| 5,135,504 A | 8/1992 | McLees |
| 5,183,468 A | 2/1993 | McLees |
| 5,215,525 A | 6/1993 | Sturman |
| 5,215,528 A | 6/1993 | Purdy et al. |
| RE34,416 E | 10/1993 | Lemieux |
| 5,273,540 A | 12/1993 | Luther et al. |
| 5,300,045 A | 4/1994 | Plassche, Jr. |
| 5,334,158 A | 8/1994 | McLees |
| 5,419,766 A | 5/1995 | Chang et al. |
| 5,458,658 A | 10/1995 | Sircom |
| 5,558,651 A | 9/1996 | Crawford et al. |
| 5,697,907 A | 12/1997 | Gaba |
| 6,004,294 A | 12/1999 | Brimhall et al. |
| 6,117,108 A | 9/2000 | Woehr et al. |
| 6,203,527 B1 | 3/2001 | Zadini et al. |
| 6,210,373 B1 | 4/2001 | Allmon |
| 6,224,569 B1 | 5/2001 | Brimhall |

FOREIGN PATENT DOCUMENTS

| WO | 99/08742 A1 | 2/1999 |
| WO | 00/69501 A1 | 11/2000 |

Primary Examiner—Manuel Mendez
Assistant Examiner—Mark K. Han
(74) Attorney, Agent, or Firm—Wood, Herron & Evans, LLP

(57) ABSTRACT

An intravenous catheter introducer assembly having a safety feature to prevent accidental needle sticks. The introducer assembly includes a needle assembly having a groove disposed on its outer surface. The introducer includes a protector made of a hollow member having an open distal end and a inwardly disposed resilient flange disposed thereon. The protector is coaxially slidably disposed around the needle with the flange abutting the outer surface of the needle and adapted to engage the groove when a catheter assembly is removed from the needle assembly.

29 Claims, 10 Drawing Sheets

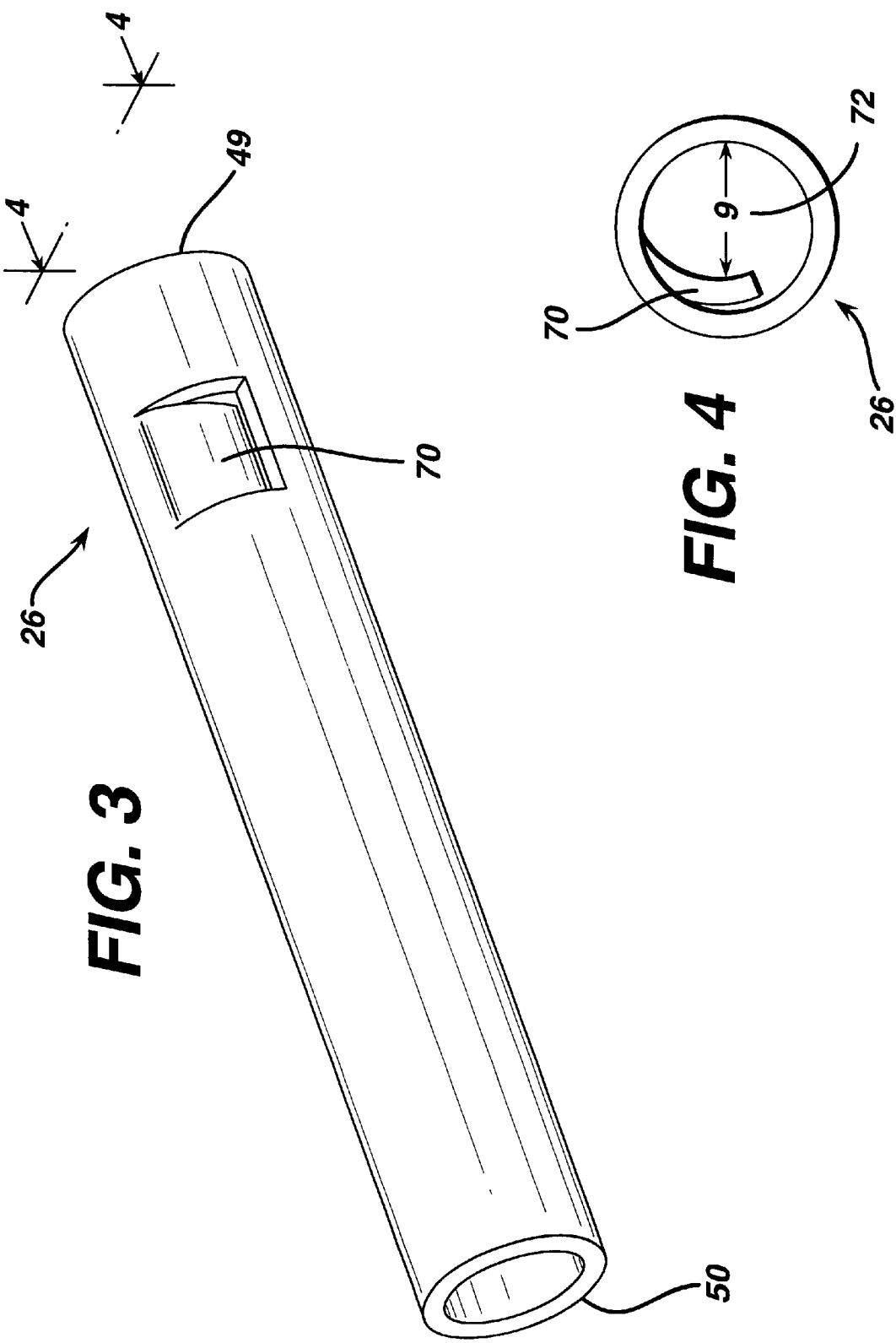

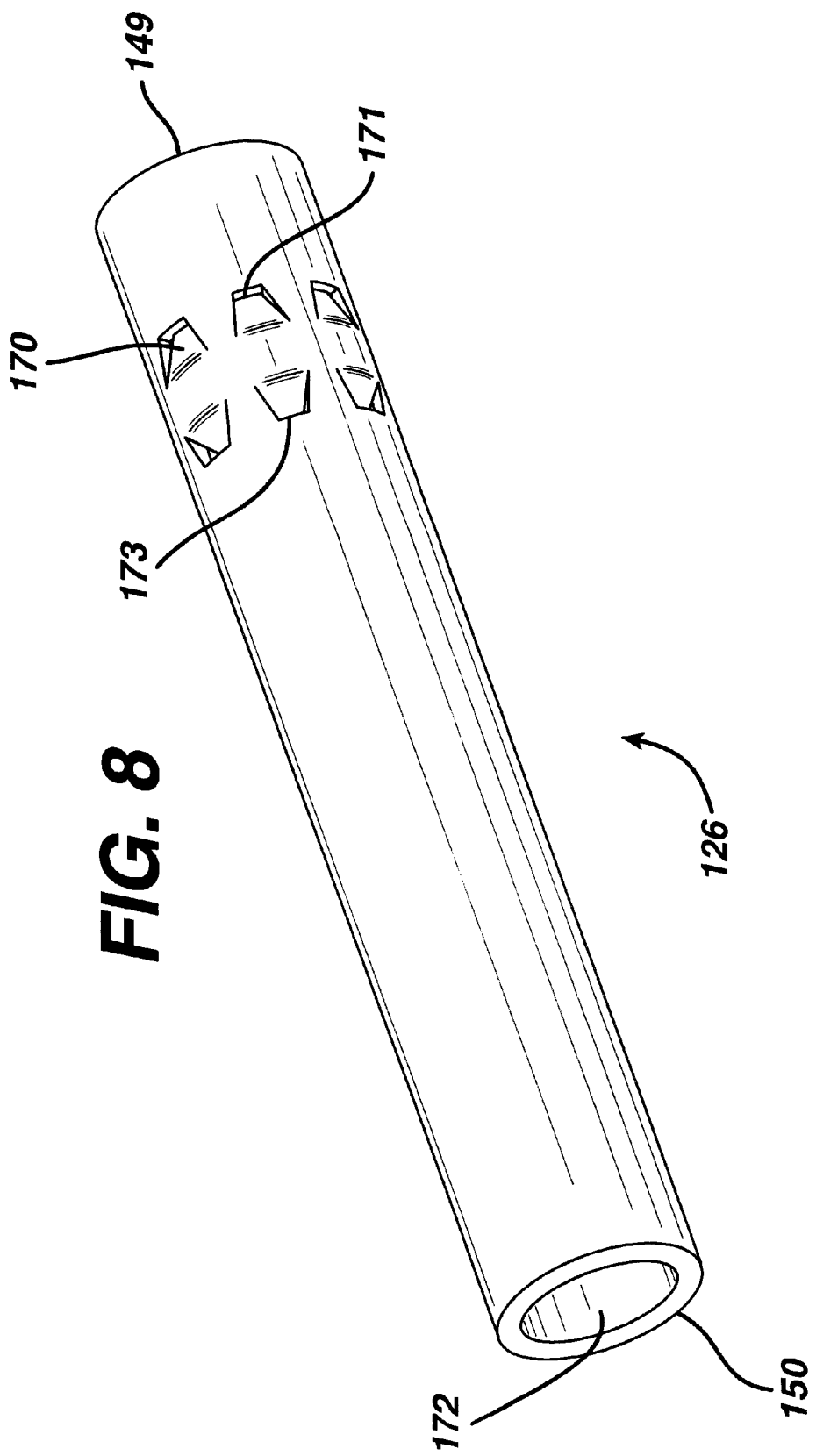

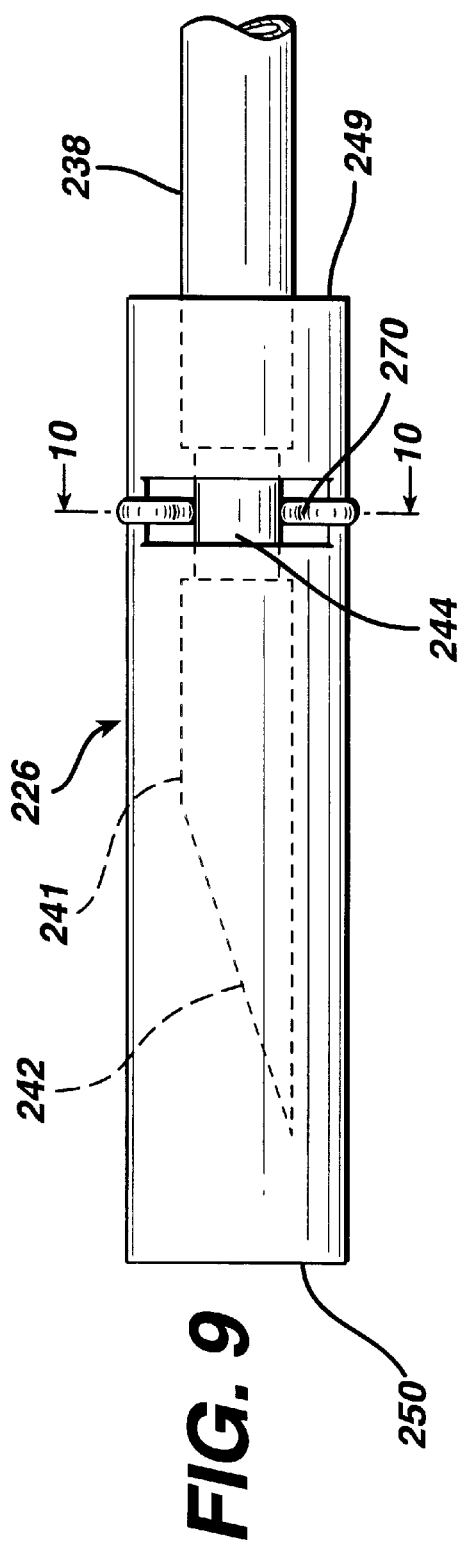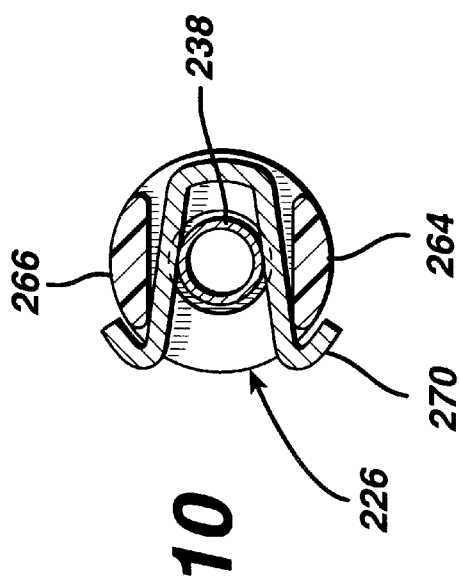

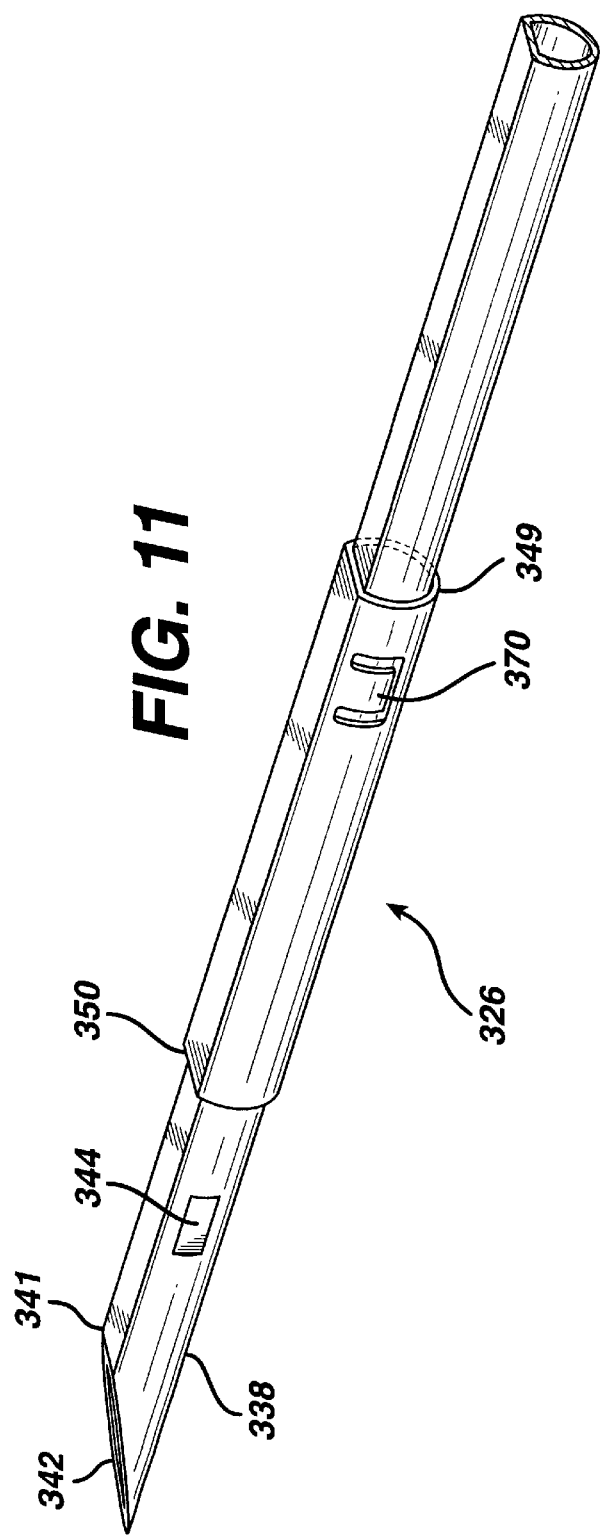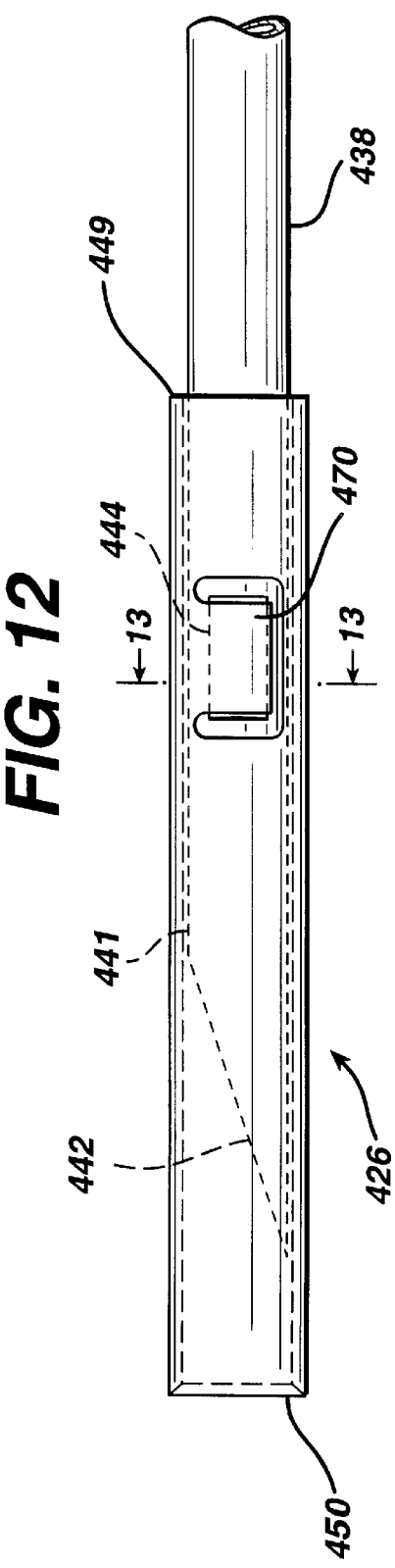

CATHETER INTRODUCER ASSEMBLY HAVING SAFETY SHIELDED NEEDLE

FIELD OF THE INVENTION

The present invention relates, in general, to intravenous (IV) catheters and, more particularly, to a safety IV catheter with a needle tip protector that will automatically cover the needle tip upon needle withdrawal.

BACKGROUND OF THE INVENTION

An intravenous (IV) catheter is an instrument that is used to introduce certain fluids such as saline solution directly into the bloodstream of a patient. Typically, a needle or other stylet is first introduced through the cannula portion of the catheter and into the skin of the patient at the desired location such as the back of the patient's hand or a vessel on the inside of the arm. Once insertion is complete, the needle is removed from the cannula portion of the catheter. After removing the needle, a fluid handling device such as a syringe is attached to the luer fitting located at the proximal end of the catheter hub. Fluid then flows directly from the fluid handling device through the catheter into the bloodstream of the patient.

When the needle is removed from the cannula, the health care worker must place the exposed needle tip at a nearby location while simultaneously addressing the task required to accomplish the needle removal. It is at this juncture that the exposed needle tip creates a danger of an accidental needle stick occurring which leaves the health care worker vulnerable to the transmission of various, dangerous blood-borne pathogens such as human immune virus (HIV) and hepatitis.

The risk of a contaminated needle stick is not just isolated to the health care worker inserting the intravenous catheter. Careless disposal of used needles can put other health care workers at risk as well. Even others outside the health care profession, for example those involved in the clean-up and final disposal of medical waste, are at risk of an accidental needle stick from a carelessly discarded needle.

The danger to health care workers and others outside the health care profession from accidental needle sticks has yielded the development of catheters with safety mechanisms in which the occurrence of such accidental needle sticks is prevented. An example of a catheter having a safety mechanism is disclosed in U.S. Pat. No. Re. 34,416 issued to Lemieux. A safety catheter is described which includes an element that covers the needle tip upon removal of the needle from the catheter. The safety element includes a split flange at its proximal end which is expanded by the needle as the needle is inserted into an undersized hole at the center of this flange. The safety element is thus held secure within the catheter hub by inserting the needle through the undersized hole which forces the outside perimeter of the split flange against the inside wall of the catheter hub. One of the drawbacks to this design is the amount of friction force exerted against the needle by the split flange. A tight fit of the flange against the catheter wall causes great friction against the needle making it difficult to be withdrawn from the catheter by the clinician. A lose fit leaves the flange prone to releasing prematurely from the catheter as the needle is withdrawn, creating the potential that the needle tip will be left exposed.

Another example of a catheter having a safety mechanism is disclosed in U.S. Pat. No. 6,117,108 issued to Woehr et al. A safety IV catheter is described including a resilient needle guard which protects the needle tip upon removal of the needle from the catheter hub. The needle guard includes an arm that includes an opening through which a needle passes causing axial movement of the arm. This axial movement forces the arm into a groove or behind a rib located on the inside of the catheter hub, capturing the needle guard in the catheter hub. A potential issue with this design develops when the needle guard is not properly seated into the catheter hub. If the distal end of the needle guard arm is not in alignment with the groove in the catheter hub, excessive forces are placed on the needle causing a high drag force as the clinician removes the needle. And, since the needle guard arm is not properly seated in the groove, it may prematurely release from the catheter hub upon the removal of the needle leaving the needle tip exposed.

The prior art safety catheters all exhibit one or more drawbacks that have thus far limited their usefulness and full acceptance by health-care workers. What is needed therefore is a safety IV catheter that functions reliably, is easy and inexpensive to manufacture, and easy to use.

SUMMARY OF THE INVENTION

An intravenous catheter introducer assembly having a safety feature to prevent accidental needle sticks. The introducer assembly includes a needle assembly having an elongated hollow tubular needle with a proximal end attached to a catheter hub and a distal end extending therefrom. The needle has a groove disposed on its outer surface. The introducer includes a protector made of a hollow member having an open distal end and a inwardly disposed resilient flange disposed thereon. The protector is coaxially slidably disposed around the needle with the flange abutting the outer surface of the needle. The introducer also includes a catheter assembly having an elongated hollow tubular catheter with a proximal end attached to a catheter hub and a distal end extending therefrom. The catheter is coaxially disposed about the needle. The catheter hub has a retainer for keeping the protector within the catheter hub until the catheter assembly and needle assembly are separated wherein the flange engages the groove and secures the protector to the needle such that the open distal end of the protector is distal to the distal end of the needle.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a perspective view of the needle tip protector of the present invention;

FIG. 4 is a view of FIG. 3 taken along line 4—4 illustrating the tab of the present invention.

FIG. 8 is a perspective view of an alternate embodiment of the needle tip protector.

FIG. 9 is a side view of another alternate embodiment of the needle tip protector shown as removed from the catheter hub and illustrating the needle tip covered by the protector.

FIG. 10 is a cross-sectional view taken along line 10—10 of FIG. 9 showing the clip which locks the needle tip protector over the needle tip.

FIG. 11 is a perspective view of another alternate embodiment of the needle tip protector shown with the needle inserted therethrough.

FIG. 12 is a side view of another alternate embodiment of a non-circular needle tip protector which illustrates the needle tip covered by the protector.

DETAILED DESCRIPTION OF THE INVENTION

As used herein, the term "proximal" refers to a location on the catheter and needle assembly with needle tip protector closest to the clinician using the device and thus furthest from the patient on which the device is used. Conversely, the term "distal" refers to a location farthest from the clinician and closest to the patient.

Figure 1:
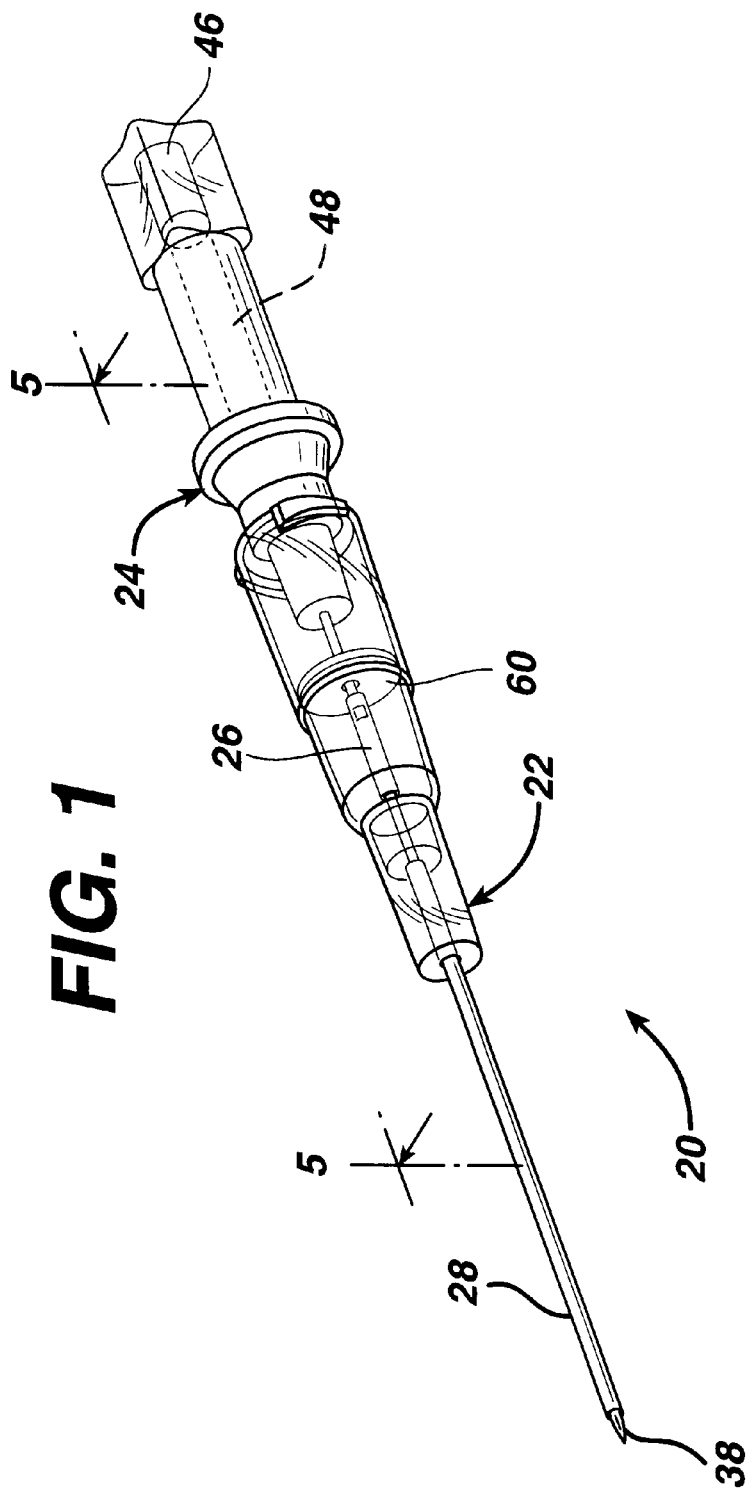
FIG. 1 is a perspective view of the catheter and needle assembly of the present invention.
Figure 2:
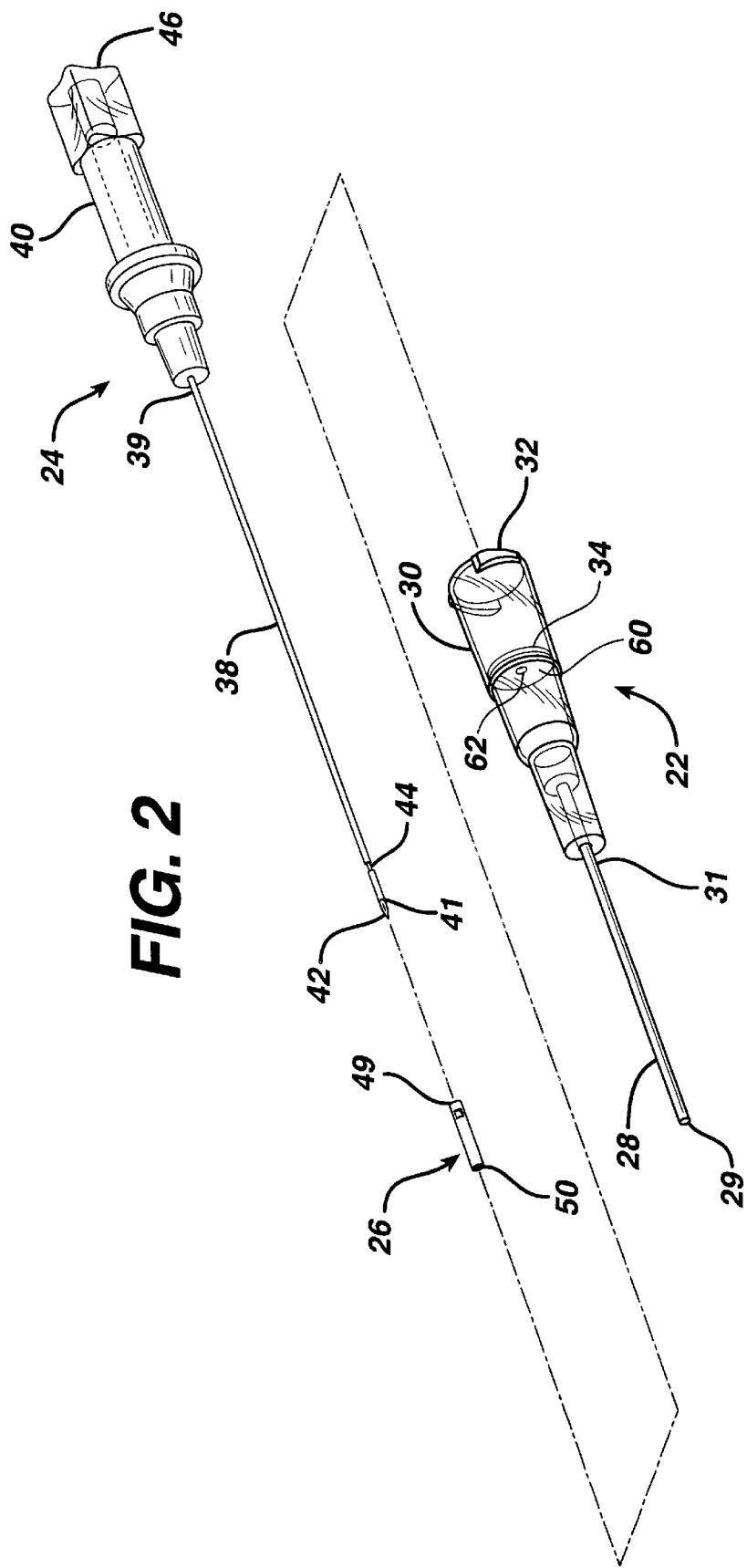
FIG. 2 is an exploded perspective view of the catheter assembly and needle assembly including the needle tip protector of the present invention
Figure 5:
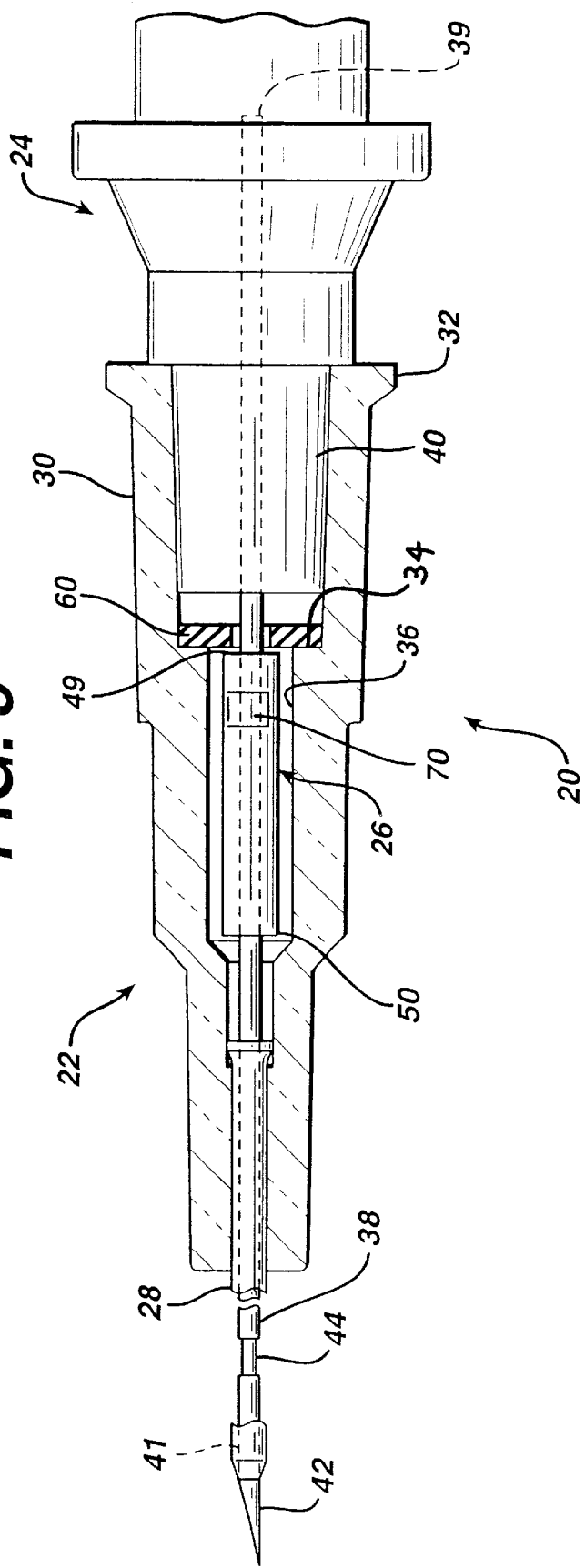
FIG. 5 is a section view of the catheter assembly and needle assembly taken along line 5—5 of FIG. 1.

As illustrated in FIGS. 1 and 2, IV catheter assembly 20 comprises catheter assembly 22 and needle assembly 24. Needle assembly 24 further includes protector 26. Catheter assembly 22 includes catheter 28 which is a tubular structure having a proximal end 31 and distal end 29. Proximal end 31 of catheter 28 is fixedly attached to catheter hub 30. Catheters are well known in the medical art and one of many suitable materials, most of which are flexible thermoplastics, may be selected for use in catheter 28. Such materials may include, for example, polyurethane or fluorinated ethylene propylene. Catheter hub 30 is a generally tubular structure having an internal cavity in fluid communication with the internal lumen of catheter 28. Catheter hub 30 may be made from a suitable, rigid medical grade thermoplastic such as, for example, polypropylene or polycarbonate. For illustration purposes catheter hub 30 is shown translucent, though in actual use it may be translucent or opaque. At the proximal end of catheter hub 30 is integrally attached Luer fitting 32, commonly known in the medical art. Luer fitting 32 provides for secure, leak proof attachment of tubing, syringes, or any of many other medical devices used to infuse or withdraw fluids through catheter assembly 22. As shown in FIGS. 1, 2, and 5, retainer 60, which is located approximately mid way between the proximal end and distal end of sidewall 36 and fixedly attached thereto as at shoulder 34, includes aperture 62 which is an opening therethrough. Retainer 60 is generally a doughnut shaped washer made of a material such as, for example, silicone or any other flexible material known to those skilled in the art. As will be described in more detail later, retainer 60 plays an important role in securing protector 26 in catheter hub 30.

Referring again to FIGS. 1 and 2, needle assembly 24 comprises needle 38, which is a tubular structure with proximal end 39 and distal end 41, needle hub 40, and protector 26. Protector 26 is assembled slidably on needle 38. Needle 38 which is preferably made of stainless steel has a lumen therethrough created by its inner diameter. Proximal end 39 of needle 38 is fixedly attached to needle hub 40. Bevel 42 which is located at distal end 41 of needle 38 creates a sharp piercing tip. Needle groove 44, which includes proximal wall 43 and distal wall 45, is located at distal end 41 of needle 38 proximal to bevel 42 and is smaller in diameter than the nominal outer diameter of needle 38. Needle groove 44 can be created by any number of means known to those skilled in the art. One such method is by machine grinding around the outside diameter of needle 38 resulting in an annular channel between its nominal outer diameter and inner diameter. Machine grinding is a process well known in the metal forming art. The resulting groove 44 is smaller in dimension than the nominal outer diameter of needle 38 but greater in dimension that the lumen in needle 38 and is important in preventing the complete removal of protector 26 from needle 38, as will be described in more detail later. In the preferred embodiment, the dimension across groove 44 is 0.002–0.003 inches smaller than the dimension of the nominal outer diameter of needle 38, dependent upon needle "gauge" size.

Needle hub 40 is generally a tubular structure having an internal cavity in fluid communication with the lumen in needle 38. It is preferably made of a translucent or transparent generally rigid thermoplastic material such as, for example, polycarbonate. At the most proximal end of the internal cavity in needle hub 40 is fixedly attached porous plug 46. A flashback chamber 48 is created in the cavity distal to porous plug 46. Porous plug 46 contains a plurality of microscopic openings which are large enough to permit the passage of air and other gasses but small enough to prevent the passage of blood. Flashback chamber 48 fills with blood upon successful entry of the needle tip into the targeted vein, providing the clinician visual conformation of the correct placement of the needle.

Referring now to FIGS. 3 and 4, protector 26 has a proximal end 49 and a distal end 50 and is preferably a hollow tubular structure with cavity 72 therethrough formed from a single piece of thin, resilient material such as, for example, stainless steel or a polymer. Located distal to proximal end 49 of protector 26 is resilient flange 70. Flange 70 includes a proximal wall and a distal wall. The longitudinal width of flange 70, the distance between the proximal wall and the distal wall, is less than the longitudinal width of needle groove 44 and is important in preventing the complete removal of protector 26 from needle 38, as will be described in more detail later. As shown in FIG. 4, resilient flange 70 is biased into cavity 72 of protector 26 resulting in dimension "a" which, when the flange 70 is in its relaxed unrestrained condition, is less than the nominal outer diameter of needle 38, permitting for a very close but slidable fit of protector 26 over needle 38.

Figure 6:
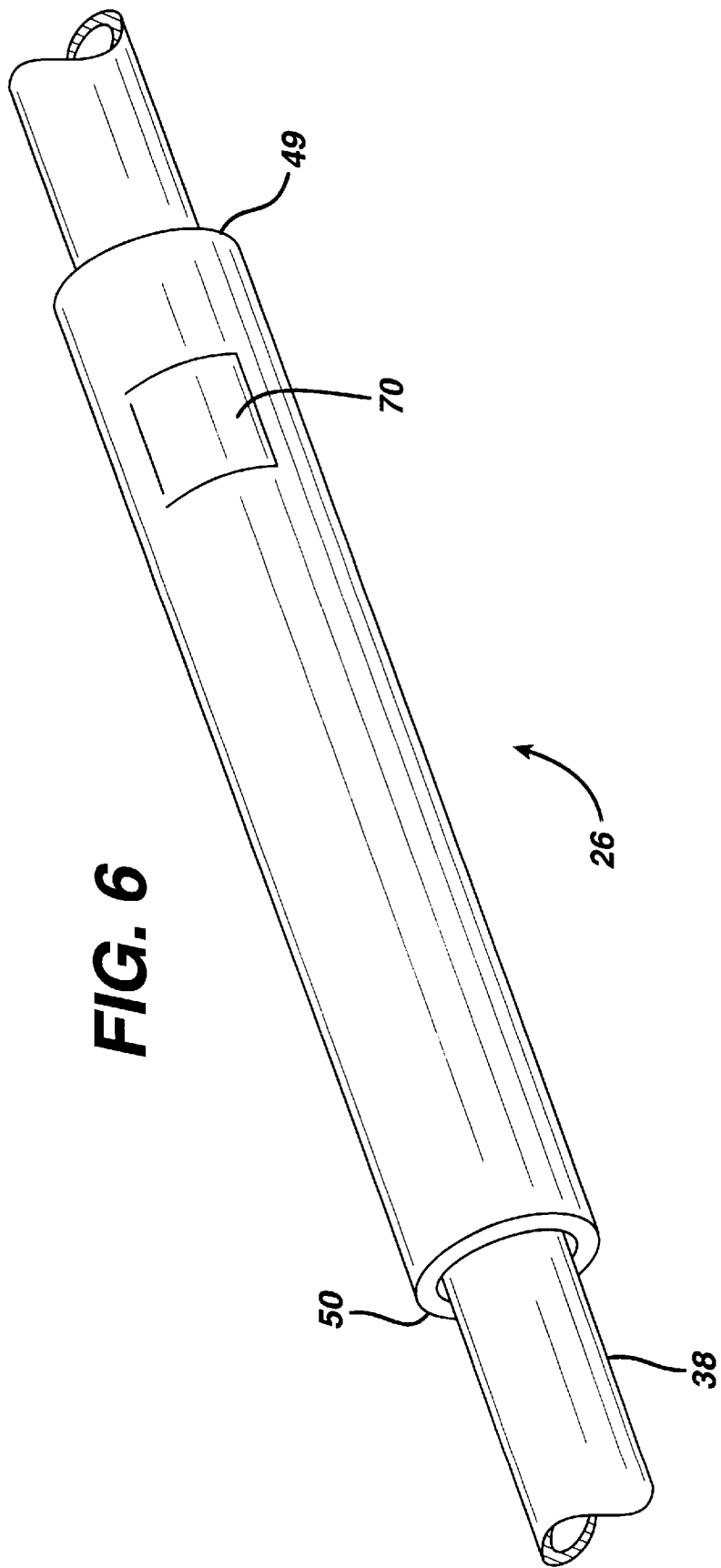
FIG. 6 is a perspective view of the needle tip protector with the needle inserted therethrough shown prior to locking the protector over the needle tip.
Figure 7:
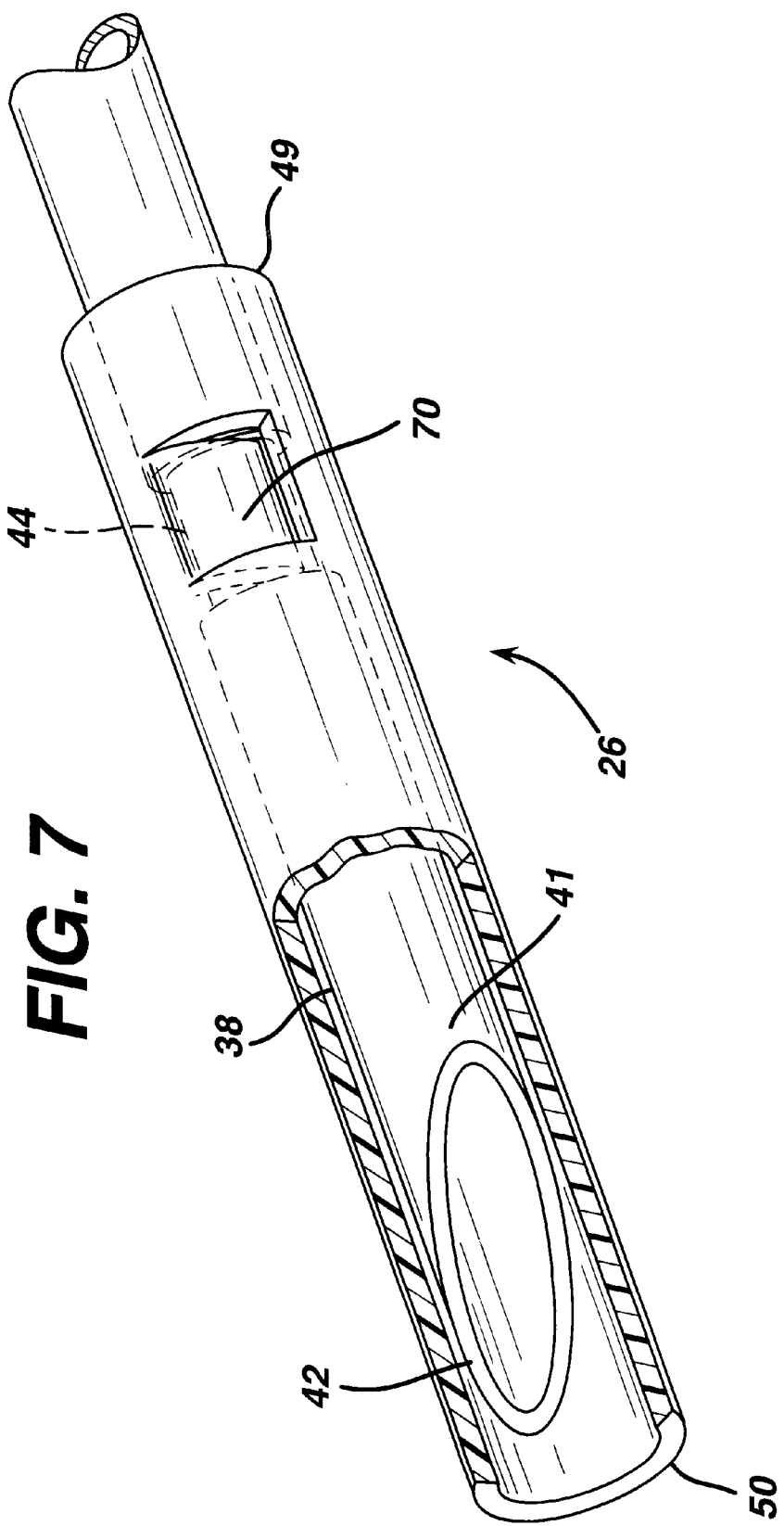
FIG. 7 is a perspective view of the needle tip protector shown as locked onto the needle after removal from the catheter hub and illustrating the needle tip covered by the protector.

Referring now to FIGS. 5–7, it can understood how protector 26 is assembled to needle 38. The proximal end of needle 38 is fixedly attached to the distal end of needle hub 40, which contains porous plug 46 fixedly attached to its proximal end. The distal end of needle 38 is inserted through proximal end 49 of protector 26 and then advanced through cavity 72, moving from proximal to distal. Flange 70 is flexed, as a result of its resilient property, so that needle 38 will pass through cavity 72 of protector 26. Needle groove 44 is located at the distal end of needle 38 just proximal to bevel 42. Groove 44 decreases the diameter of needle 38 locally to a dimension smaller than the nominal outer diameter of needle 38. When needle 38 is retracted, flange 70 locks into groove 44 preventing the complete removal of protector 26 from the distal end of needle 38.

As shown in FIG. 1, needle assembly 24, including protector 26, is assembled into catheter assembly 22. Distal end 41 of needle 38 extends distally from distal end 29 of catheter 28. Protector 26 is held distal to retainer 60 inside the cavity in catheter hub 30 by aperture 62, which has a diameter smaller in dimension than the outer diameter of protector 26. Protector 26 is also located proximal to catheter 28, which has an inner diameter smaller than the outer diameter of protector 26 preventing any further distal movement. Needle assembly 22 is secured onto luer fitting 32 of catheter hub 30.

Now, it will be described how in actual clinical use, the IV catheter assembly 20 of the present invention functions. The distal end of needle 38 which extends just past the distal end of catheter 28 is inserted into the patient's vein. The clinician observes blood in the flash chamber in needle hub 40. The clinician grasps needle hub 40, and catheter assembly 22 alone is moved distally into the vein. The clinician applies slight pressure to the insertion site to hold catheter assembly 22 secure. The clinician grasps needle hub 40 and begins withdrawal of needle assembly 24 from catheter assembly 22. During this process, protector 26 remains secure inside catheter hub 30 until groove 44 on needle 38 comes into contact with flange 70. Prior to groove 44 encountering flange 70, retainer 60 blocks any further proximal movement of protector 26. During withdrawal, needle 38 is retracted proximally into catheter 28 and catheter hub 30. When groove 44 of needle 38 comes into contact with flange 70 of protector 26, the distance between proximal wall 71 and distal wall 73 of flange 70 which is less than the distance between proximal wall 43 and distal wall 45 of groove 44 causes flange 70 which is biased into cavity 72 to engage into groove 44 thus locking protector 26 on needle 38. After flange 70 locks into groove 44, continued proximal movement of needle 38 carries protector 26 proximal as well, forcing proximal end 49 of protector 26 against retainer 60. When enough force is applied by protector 26, aperture 62 dilates due to the resilient property of retainer 60, permitting continued movement proximal, past retainer 60. Needle assembly 24 is now removed entirely from catheter assembly 22, with the needle tip covered by protector 26 of the present invention.

A first alternate embodiment of the present invention is shown in FIG. 8. In this embodiment, protector 126, similar to protector 26, is generally hollow tubular structure formed from a single piece of thin, resilient material such as, for example, stainless steel or a polymer. This embodiment has a plurality of flanges 170. Flanges 170 are located distal to proximal end 149 of protector 126. Flanges 170 create proximal walls 171 and distal walls 173 and are biased into cavity 172 of protector 126.

A second alternate embodiment of the present invention is shown in FIG. 9. In this embodiment, protector 226, similar to protector 26, includes clip 270. Clip 270, which functions to replace flange 70 in the preferred embodiment, is slidably assembled to protector 226. Clip 270 is preferably made of a resilient material such as, for example, stainless steel, or any other suitable material known to those skilled in the art. As shown in FIG. 10, clip 270 is generally a U-shaped wireform secured to protector 226 by bridges 264 and 266.

FIG. 11 shows a third alternate embodiment where protector 326 is a hollow tubular structure preferably formed from a single piece of thin, resilient material such as for example, stainless steel or a polymer. In this embodiment, protector 326 has a flat formed on one side along its entire length. Located distal to proximal end 349 of protector 326 is flange 370, similar to flange 70. Needle notch 344, which functions to replace needle groove 44, is an indentation in needle 338. In this embodiment, the depth from surface 347 of needle notch 344 to the outer surface of needle 338 is 0.002–0.003 inches, dependent upon needle "gauge" size. However, the depth from surface 347 of needle notch 344 to the outer surface of needle 338 could be larger than 0.003 inches possibly exposing the lumen of needle 338. Needle notch 344 locks with flange 370 preventing the complete removal of protector 326 from distal end 341 of needle 338. To ensure the alignment of flange 370 with notch 344, needle 338 also has a flat along its entire length which takes the shape of protector 326 to prevent any axial movement of needle 338 in protector 326. Needle notch 344 could be a single indentation in needle 338 or multiple indentations possibly spaced 180° apart. Similarly, protector 326 could contain a single flange or multiple flanges possibly spaced 180° apart.

Figure 13:
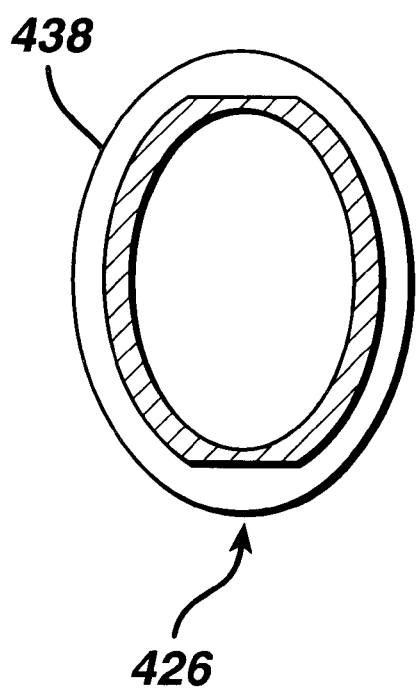
FIG. 13 is a cross-sectional view taken along line 13—13 of FIG. 12 of the non-circular needle and needle tip protector.

FIGS. 12 and 13 shows a fourth alternate embodiment of the present invention. In this embodiment, protector 426 is a hollow non-circular tubular structure preferably formed from a single piece of thin, resilient material such as, for example, stainless steel or a polymer. Located distal to proximal end 449 of protector 426 is flange 470, similar to flange 370. Needle notch 444, similar to notch 344, functions to replace needle groove 44. Needle notch 444 is an indentation in needle 438 which locks with flange 470 preventing the complete removal of protector 426 from distal end 441 of needle 438. In this embodiment, the depth from surface 447 of needle notch 444 to the outer surface of needle 438 is 0.002–0.003 inches, dependent upon needle "gauge" size. However, the depth from surface 447 of needle notch 444 to the outer surface of needle 438 could be larger than 0.003 inches possibly exposing the lumen of needle 438. To ensure the alignment of flange 470 with notch 444, needle 438 is also non-circular taking the shape of protector 426 to prevent any axial movement of needle 438 in protector 426. Needle notch 444 could be a single indentation in needle 438 or multiple indentations possibly spaced 180° apart. Similarly, protector 426 could contain a single flange or multiple flanges possibly spaced 180° apart.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims. In addition, it should be understood that every structure described above has a function and such structure can be referred to as a means for performing that function.

What is claimed is:

1. An intravenous catheter introducer assembly having a safety feature to prevent accidental needle sticks, said introducer assembly comprising:
   a. a needle assembly comprising an elongated hollow tubular needle having a proximal end attached to a needle hub, a distal end extending therefrom, and a lumen running therebetween, said needle having a groove disposed on an outer surface thereof between said distal and proximal ends, the outer surface of the needle immediately proximal to the groove having a first diameter, the outer surface of the needle immediately distal to the groove having a second diameter substantially equal to the first diameter;
   b. a protector comprising a hollow member having an open distal end and an inwardly disposed resilient flange disposed thereon, said protector is coaxially slidably disposed around said needle with said flange abutting said outer surface of said needle; and
   c. a catheter assembly comprising an elongated hollow tubular catheter having a proximal end attached to a catheter hub and a distal end extending therefrom, said catheter coaxially disposed about said needle, said catheter hub having a retainer for keeping said protector within said catheter hub until said catheter assembly and needle assembly are separated wherein said flange engages said groove and secures said protector to said needle such that said open distal end of said protector is distal to said distal end of said needle.

2. The introducer assembly of claim 1 wherein said protector comprises a cylindrical tubular member having open proximal and distal ends and an inwardly disposed flange disposed therebetween.

3. The introducer assembly of claim 1 wherein said protector comprises a cylindrical tubular member having open proximal and distal ends having a plurality of inwardly disposed flanges disposed therebetween.

4. The introducer assembly of claim 3 wherein said plurality of inwardly disposed flanges are arranged concentrically about said protector.

5. The introducer assembly of claim 1 wherein said needle and said protector have non-circular cross sections such that said protector cannot rotate with respect to said needle.

6. The introducer assembly of claim 1 wherein said groove on said needle is a concentric groove running around a circumference of said needle without penetrating into said lumen.

7. The introducer assembly of claim 1 wherein said groove on said needle comprises a notch cut into said needle exposing said lumen.

8. The introducer assembly of claim 1 wherein the needle is cylindrical.

9. The introducer assembly of claim 1, the flange being defined by an integral portion of the protector member.

10. An intravenous catheter introducer assembly having a safety feature to present accidental needle sticks, said introducer assembly comprising:
    a. a needle assembly comprising an elongated hollow tubular needle having a proximal end attached to a needle hub, a distal end extending therefrom, and a lumen running therebetween, said needle having a groove disposed on an outer surface thereof between said distal and proximal ends;
    b. a protector comprising a hollow member having an open distal end and an inwardly disposed resilient flange disposed thereon, said protector is coaxially slidably disposed around said needle with said flange abutting said outer surface of said needle; and
    c. a cathether assembly comprising an elongated hollow tubular catheter having a proximal end attached to a catheter hub and a distal end extending therefrom, said catheter coaxially disposed about said needle, said catheter hub having a retainer for keeping said protector within said catheter hub until said catheter assembly and needle assembly are separated, said retainer having a resilient washer disposed concentrically within said catheter hub and fixedly attached thereto, said washer having an insider diameter less than an outside diameter of said protector, wherein said flange engages said groove and secures said protector to said needle such that said open distal end of said protector is distal to said distal end of said needle.

11. The introducer assembly of claim 10, wherein said needle is cylindrical.

12. An intravenous catheter introducer assembly having a safety feature to prevent accidental needle sticks, said introducer assembly comprising:
    a. a needle assembly comprising an elongated hollow tubular needle having a proximal end attached to a needle hub, a distal end extending therefrom, and a lumen running therebetween, said needle having a groove disposed on an outer surface thereof between said distal and proximal ends;
    b. a protector comprising a hollow member having an open distal end and an inwardly disposed resilient flange disposed thereon, said protector is coaxially slidably disposed around said needle with said flange abutting said outer surface of said needle, the protector having a constant inner diameter between said distal end and a proximal end thereof; and
    c. a catheter assembly comprising an elongated hollow tubular catheter having a proximal end attached to a catheter hub and a distal end extending therefrom, said catheter coaxially disposed about said needle, said catheter hub having a retainer for keeping said protector within said catheter hub until said catheter assembly and needle assembly are separated wherein said flange engages said groove and secures said protector to said needle such that said open distal end of said protector is distal to said distal end of said needle.

13. The introducer assembly of claim 12 wherein said protector comprises a cylindrical tubular member having open proximal and distal ends and an inwardly disposed flange disposed therebetween.

14. The introducer assembly of claim 12 wherein said protector comprises a cylindrical tubular member having open proximal and distal ends having a plurality of inwardly disposed flanges disposed therebetween.

15. The introducer assembly of claim 14 wherein said plurality of inwardly disposed flanges are arranged concentrically about said protector.

16. The introducer assembly of claim 12 wherein said needle and said protector have non-circular cross sections such that said protector cannot rotate with respect to said needle.

17. The introducer assembly of claim 12 wherein said groove on said needle is a concentric groove running around a circumference of said needle without penetrating into said lumen.

18. The introducer assembly of claim 12 wherein said groove on said needle comprises a notch cut into said needle exposing said lumen.

19. The introducer assembly of claim 12, the flange being defined by an integral portion of the protector member.

20. The introducer assembly of claim 12 wherein the needle is cylindrical.

21. An intravenous catheter introducer assembly having a safety feature to prevent accidental needle sticks, said introducer assembly comprising:

a. a needle assembly comprising an elongated hollow tubular needle having a proximal end attached to a needle hub, a distal end extending therefrom, and a lumen running therebetween, said needle having a groove disposed on an outer surface thereof between said distal and proximal ends;

b. a protector comprising a hollow member having an open distal end and an inwardly disposed resilient flange disposed thereon and extending longitudinally of the member, said protector is coaxially slidably disposed around said needle with said flange abutting said outer surface of said needle; and c. a catheter assembly comprising an elongated hollow tubular catheter having a proximal end attached to a catheter hub and a distal end extending therefrom, said catheter coaxially disposed about said needle, said catheter hub having a retainer for keeping said protector within said catheter hub until said catheter assembly and needle assembly are separated wherein said flange engages said groove and secures said protector to said needle such that said open distal end of said protector is distal to said distal end of said needle.

22. The introducer assembly of claim 21 wherein said protector comprises a cylindrical tubular member having open proximal and distal ends and an inwardly disposed flange disposed therebetween.

23. The introducer assembly of claim 21 wherein said protector comprises a cylindrical tubular member having open proximal and distal ends having a plurality of inwardly disposed flanges disposed therebetween.

24. The introducer assembly of claim 23 wherein said plurality of inwardly disposed flanges are arranged concentrically about said protector.

25. The introducer assembly of claim 21 wherein said needle and said protector have non-circular cross sections such that said protector cannot rotate with respect to said needle.

26. The introducer assembly of claim 21 wherein said groove on said needle is a concentric groove running around a circumference of said needle without penetrating into said lumen.

27. The introducer assembly of claim 21 wherein said groove on said needle comprises a notch cut into said needle exposing said lumen.

28. The introducer assembly of claim 21, the flange being defined by an integral portion of the protector member.

29. The introducer assembly of claim 21, wherein the needle is cylindrical.

\* \* \* \* \*

UNITED STATES PATENT AND TRADEMARK OFFICE
CERTIFICATE OF CORRECTION

PATENT NO.   : 6,663,592 B2
DATED        : December 16, 2003
INVENTOR(S)  : Edward A. Rhad et al.

It is certified that error appears in the above-identified patent and that said Letters Patent is hereby corrected as shown below:

Column 1,
Line 64, "A lose fit leaves" should read -- A loose fit leaves --;

Column 2,
Line 65, "of the present invention" should read -- of the present invention. --;

Column 4,
Line 2, "mid way between" should read -- midway between --;
Line 36, "greater in dimension that the lumen" should read -- greater in dimension than the lumen --;
Line 53, "visual conformation of the correct" should read -- visual confirmation of the correct --;

Column 5,
Line 6, "it can understood" should read -- it can be understood --;

Column 8,
Line 6, "safety feature to present accidental" should read -- safety feature to prevent accidental --.

Signed and Sealed this

Thirtieth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,663,592 B2
APPLICATION NO. : 09/948088
DATED : December 16, 2003
INVENTOR(S) : Edward A. Rhad et al.

Page 1 of 1

It is certified that error appears in the above-identified patent and that said Letters Patent is hereby corrected as shown below:

Column 1,
Line 64, "A lose fit leaves" should read -- A loose fit leaves --;

Column 2,
Line 33, "catheter hub" should be -- needle hub --;
Line 65, "of the present invention" should read -- of the present invention. --;

Column 4,
Line 2, "mid way between" should read -- midway between --;
Line 36, "greater in dimension that the lumen" should read -- greater in dimension than the lumen --;
Line 53, "visual conformation of the correct" should read -- visual confirmation of the correct --;

Column 5,
Line 6, "it can understood" should read -- it can be understood --;

Column 8,
Line 6, "safety feature to present accidental" should read -- safety feature to prevent accidental --.

Signed and Sealed this

Fifth Day of February, 2008

JON W. DUDAS
*Director of the United States Patent and Trademark Office*